United States Patent [19]

Meilland

[11] Plant 5,060

[45] Jun. 14, 1983

[54] ROSE PLANT — MEIROTERVI VARIETY

[75] Inventor: Marie L. Meilland, Antibes, France

[73] Assignee: The Conard-Pyle Company, West Grove, Pa.

[21] Appl. No.: 322,583

[22] Filed: Nov. 18, 1981

[30] Foreign Application Priority Data

Dec. 8, 1980 [FR] France ..... 2876

[51] Int. Cl.[3] ..... A01H 5/00

[52] U.S. Cl. ..... Plt./20

[58] Field of Search ..... Plt./20

*Primary Examiner*—James R. Feyrer

*Attorney, Agent, or Firm*—Burns, Doane, Swecker & Mathis

[57] ABSTRACT

A new and distinct variety of Hybrid Tea rose plant is provided having double flowers which are of a brilliant luminous red coloration. The new variety resulted from the crossing of the Meidirapo variety and an unnamed seedling, and is particularly suited for growing in a greenhouse to form in abundance highly attractive flowers which when cut are long lasting and hold their color well.

16 Drawing Figures

SUMMARY OF THE INVENTION

The new variety resulted from the crossing of a female parent of the Meidirapo variety (unpatented) with pollen from an unnamed male parent (also unpatented). Selective study of the offspring resulted in the identification of a single plant of the new variety.

The new variety has been found to possess:

(a) a vigorous upright growth habit, (b) the ability to form in abundance double flowers of firm petal substance which are brilliant luminous red in coloration borne on substantially straight stems and which are long lasting and substantially resistant to color change, (c) the ability to form glossy dark green foliage, and (d) the presence of a large number of thorns.

The new variety is particularly suited for growing in greenhouses to continuously produce highly attractive cut flowers. Unlike many deep red rose blossoms of other varieties, the flowers of the present variety hold their color well and do not assume a tint of blue or magenta upon the passage of time. Such flowers are well adapted to bulk production, are long lasting when cut, and ship well in transit. Also, the lustrous dark green foliage of the new variety contributes to the attractiveness of the cut flowers.

The new variety has been found to be capable of asexual propagation by the normally accepted techniques of rose propagation e.g. by budding, grafting, and cuttings. Successive generations of propagation have shown that the new variety is homogeneous, uniform, and stable.

The new variety has been named the Meirotervi variety.

BRIEF DESCRIPTION OF THE PHOTOGRAPH

The accompanying photograph shows as nearly true as it is reasonably possible to make the same in a color illustration of this character, typical specimens of plant parts obtained during February from plants growing under glass in Southern France while grafted on Rosa manettii rootstock illustrated in:

FIG. 1 — a specimen of a young shoot;

FIG. 2 — a specimen of a bud before the sepals open;

FIG. 3 — a specimen of a bud at the opening of the sepals;

FIG. 4 — a specimen of a bud at the opening of the petals;

FIG. 5 — a specimen of a flower while opening;

FIG. 6 — a specimen of a fully open flower — plan view — obverse;

FIG. 7 — a specimen of a fully open flower — plan view — reverse;

FIG. 8 — a specimen of a fully open flower immediately prior to petal drop — plan view — obverse;

FIG. 9 — a specimen of a fully open flower immediately prior to petal drop — plan view — reverse;

FIG. 10 — a specimen of a flower receptacle showing the arrangement of the pistils (sepals and stamens removed);

FIG. 11 — a specimen of a floral receptacle showing the arrangement of the stamens (sepals removed);

FIG. 12 — a portion of a main branch showing the mature wood;

FIG. 13 — a portion of a young flowering stem;

FIG. 14 — a specimen of a leaf with three leaflets — upper surface;

FIG. 15 — a specimen of a leaf with five leaflets — upper surface; and

FIG. 16 — a specimen of a leaf with seven leaflets — under surface.

DETAILED DESCRIPTION

Figures 1, 2, 3, 4, 5, 6, 7, 8, 9, 10, 11, 12, 13, 14, 15, 16:
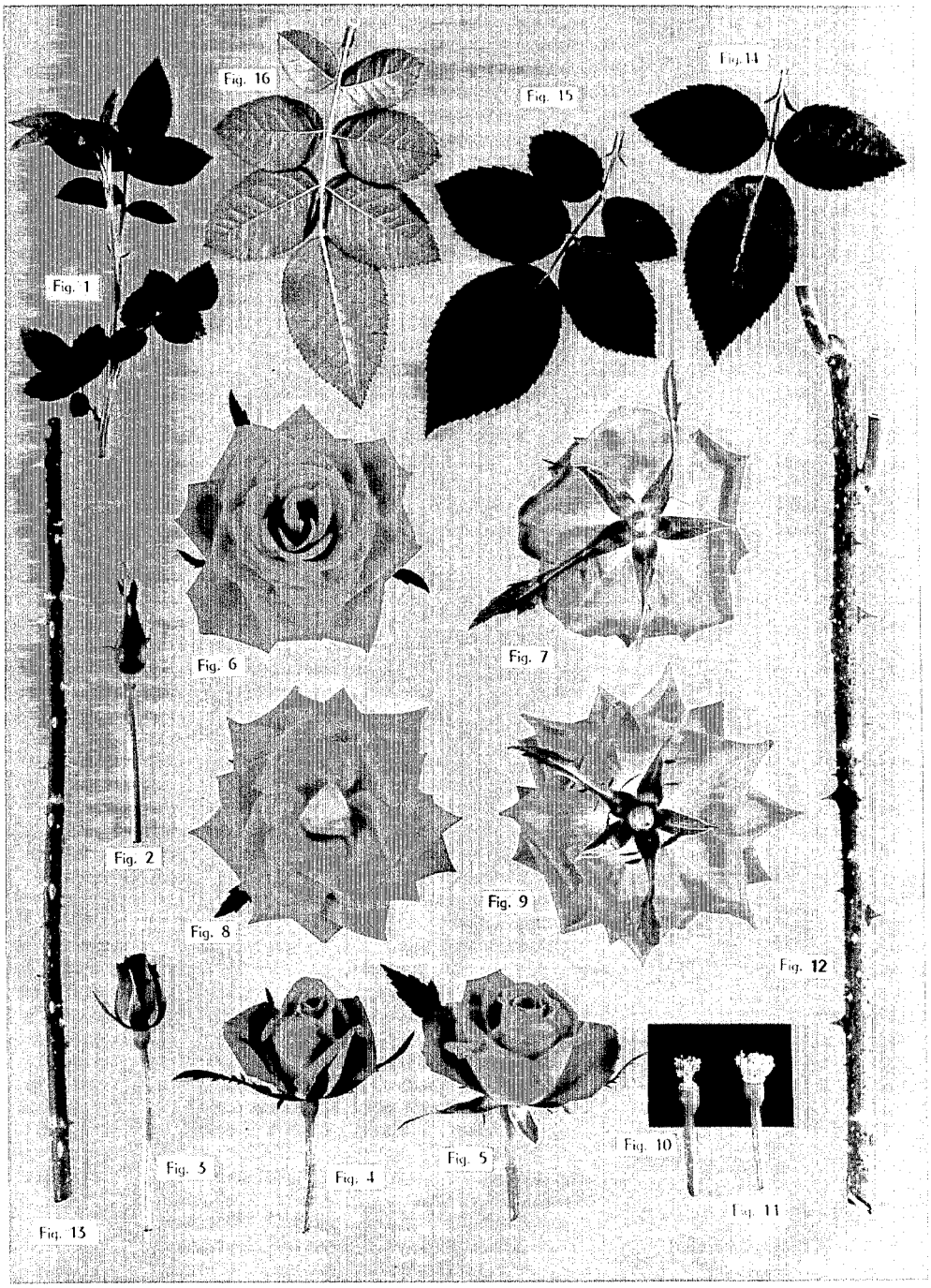

The plants described were observed during February while grafted on *Rosa manettii* rootstock and growing in a greenhouse in Southern France.

The chart utilized in the identification of the colors is that of The Royal Horticultural Society (R.H.S. Colour Chart). The terminology preceding the numbered references to this chart has been added to designate in common terms the corresponding colors.

Class: Hybrid Tea.

Plant:

*Bearing.*—Erect.

Branches:

*Color.*—Young stems: light green, Yellow-Green Group 146B, with slight shading of red. Mature wood: bronzish-green, Yellow-Green Group 146A.

*Thorns.*—Numerous as illustrated.

Foliage:

*Leaflets.*—Number: 3,5, and 7 most frequently. Shape: elliptic as illustrated.

*Color.*—Young leaves: Upper surface: dark green, Yellow-Green Group 147A. Under surface: light green, Yellow-Green Group 148C, more or less shaded with red tones. Adult leaves: Upper surface: dark green, Yellow-Green Group 147A. Under surface: light green, Yellow-Green Group 148C.

Flowers:

*Number of flowers.*—Usually one per stem, but varied culture conditions can produce more than one per stem.

*Peduncle.*—Straight and rigid, light green in color, often covered with a large number of small thorns. Length: approximately 6 to 6.5 cm. on average.

*Bud.*—Shape: oblong before the opening of the sepals. Length: approximately 3.5 cm. on average outside the calyx immediately prior to the opening of the sepals. Size: average. Color on opening: Upper surface of petal: cardinal red, slightly darker than Red Group 53A. Under surface of petal: dull cardinal red, Red Group 53A.

*Blossom.*—Diameter: approximately 11.5 cm. on average when fully open. Color — when first opening: Upper surface: cardinal red, Red Group 53A suffused with Red Group 46A with luminous qualities. Under surface: dull cardinal red, Red Group 53A. Color — during the course of opening: Upper surface: very luminous, Red Group 46A. Under surface: dull cardinal red, Red Group 53B. Color — immediately prior to petal drop: Upper surface: very luminous, Red Group 46A on the external petals and Red Group 46B on the internal petals. Under surface: dull Red Group 53B on the external petals and Red Group 53C on the internal petals. Fragrance: no appreciable scent. Vase life: very long. Petals: very firm, and approximately 30 to 40 on average. Stamens: approximately 93 on average, anthers are yellowish. Pistils: approximately 80 on average, umber colored. Stigmas: whitish. Styles: greenish with a light tint of fuchsia. Receptacle: light green.

Development:

*Vegetation.*—Very vigorous.

*Flowering.*—Continuously produces flowers in abundance in a greenhouse environment.

*Forcing ability.*—Very good.

*Resistance to diseases.*—Very good.

I claim:

1. A new and distinct variety of Hybrid Tea rose plant, substantially as illustrated and described, having (a) a vigorous upright growth habit, (b) the ability to form in abundance double flowers of firm petal substance which are brilliant luminous red in coloration borne on substantially straight stems and which are long lasting and substantially resistant to color change, (c) the ability to form glossy dark green foliage, and (d) the presence of a large number of thorns.

* * * * *